(12) United States Patent
Sapey-Triomphe et al.

(10) Patent No.: US 12,251,677 B2
(45) Date of Patent: Mar. 18, 2025

(54) PRILLS OF HYDROQUINONE AND METHOD FOR OBTAINING THE SAME

(71) Applicant: SPECIALTY OPERATIONS FRANCE, Lyons (FR)

(72) Inventors: Rodolphe Sapey-Triomphe, Sérézin-du-Rhône (FR); Lars Fischer, Vienne (FR); David Vanzin, Franklin, TN (US)

(73) Assignee: SPECIALTY OPERATIONS FRANCE, Lyons (FR)

( * ) Notice: Subject to any disclaimer, the term of this patent is extended or adjusted under 35 U.S.C. 154(b) by 709 days.

(21) Appl. No.: 17/295,691

(22) PCT Filed: Dec. 3, 2019

(86) PCT No.: PCT/EP2019/083557
§ 371 (c)(1),
(2) Date: May 20, 2021

(87) PCT Pub. No.: WO2020/115078
PCT Pub. Date: Jun. 11, 2020

(65) Prior Publication Data
US 2021/0387151 A1    Dec. 16, 2021

Related U.S. Application Data

(60) Provisional application No. 62/774,513, filed on Dec. 3, 2018.

(51) Int. Cl.
*B01J 2/02* (2006.01)
*B01J 2/20* (2006.01)
*C07C 39/08* (2006.01)

(52) U.S. Cl.
CPC . *B01J 2/20* (2013.01); *B01J 2/02* (2013.01); *C07C 39/08* (2013.01)

(58) Field of Classification Search
CPC ................................. C07C 39/08; B01J 2/02
See application file for complete search history.

(56) References Cited

U.S. PATENT DOCUMENTS

| 7,235,299 | B2* | 6/2007 | Le Thiesse | C07C 50/04 |
|---|---|---|---|---|
| | | | | 428/407 |
| 11,046,631 | B2* | 6/2021 | Humblot | B01J 2/20 |
| 2006/0135730 | A1* | 6/2006 | Le Thiesse | G03C 7/39216 |
| | | | | 528/86 |
| 2009/0306436 | A1 | 12/2009 | Gayet et al. | |
| 2009/0324952 | A1 | 12/2009 | Le Thiesse | |
| 2020/0031749 | A1* | 1/2020 | Humblot | C07C 39/08 |

FOREIGN PATENT DOCUMENTS

| DE | 202018005859 U1 | 3/2019 |
|---|---|---|
| JP | 2000-302716 A2 | 1/2000 |
| WO | 2001/70869 A2 | 9/2001 |

(Continued)

*Primary Examiner* — Hoa (Holly) Le
(74) *Attorney, Agent, or Firm* — Osha Bergman Watanabe & Burton

(57) ABSTRACT

The present invention relates to new lightly colored prills of hydroquinone. More particularly, the invention provides a new method for preparing said lightly colored prills of hydroquinone. The invention also relates to said prills of hydroquinone obtained by said new method.

16 Claims, 2 Drawing Sheets

(56) References Cited

FOREIGN PATENT DOCUMENTS

| WO | 2004/039758 A1 | 5/2004 |
| WO | 2008/000955 A1 | 1/2008 |
| WO | 2008/000956 A1 | 1/2008 |
| WO | 2016/033157 A1 | 3/2016 |
| WO | 2018153913 A1 | 8/2018 |

* cited by examiner

PRILLS OF HYDROQUINONE AND METHOD FOR OBTAINING THE SAME

This application is a U.S. national phase entry under 35 U.S.C. § 371 of International Application No. PCT/EP2019/083557, filed on Dec. 3, 2019, which claims priority to U.S. Provisional Application No. 62/774,513, filed on Dec. 3, 2018. The entire contents of these applications are explicitly incorporated herein by this reference.

TECHNICAL FIELD OF THE INVENTION

The present invention relates to new white or lightly colored prills of hydroquinone. More particularly, the invention provides a new method for preparing said lightly colored prills of hydroquinone. The invention also relates to said prills of hydroquinone obtained by said new method.

BACKGROUND OF THE INVENTION

Among diphenol compounds, hydroquinone (HQ) is a product that is widely used in many fields as antioxidant in elastomers, polymerization inhibitor or as a monomer for polymer production. Thus, it is a product that is used in large quantities.

Currently, hydroquinone is commercially available in different forms, mainly as crystal powder, or flakes. For instance, the patent document WO 2016/033157 discloses methods for making powders of crystallized hydroquinone particles. However, the powder is formed of small and brittle needles. The disadvantages which result therefrom are the presence of fine particles, which cause problems of dust formation during storage, transportation and physical handling and movement of said powder. Even with reduced agglomeration tendencies, hydroquinone powders may still be harmful to the environment and individuals because of the risks of dust explosion and because of the toxicological properties of this substance.

Alternative forms have been disclosed. Japanese patent JP 2000-302716 A discloses a technique for granulating hydroquinone, which consists of passing hydroquinone powder between two rolls to produce tablets, then crushing the tablets to obtain granules. The disadvantage of that process is that dust can subsist in the granulated product either because of the passage through the rollers, breaking the crystals in the rollers of the compacter, or by wear of the tablets in the crusher. Further, the granules are compact and their rate of dissolution is very low compared with the initial powder. Additionally, the granules may cake or clump upon storage and be difficult to process and transport in processing equipment. The granules may also be prone to attrition during handling.

The patent document WO 2001/70869 discloses the preparation of granules of at least one sterically hindered phenol antioxidant using an organic processing agent. Said organic processing agent is mixed with said antioxidant to form a paste, which is processed to form granules, and said granules are finally dried to remove the organic processing agent without melting the antioxidant. One problem of this method is that the final antioxidant granules may still comprise some undesired traces of the organic processing agent.

The patent documents WO 2008/000955 & WO 2008/00956 discloses a hydroquinone in flake form, and process for obtaining it.

The patent document WO 2004/039758 discloses hydroquinone beads (also called "pearls"), which are highly spherical solid particles. These hydroquinone beads are said to be devoid of dust and have a physical form which confers on them good resistance to attrition. The process for the preparation of said beads consists in preparing, under hot conditions, a concentrated aqueous solution of hydroquinone, in then fragmenting the solution into droplets by passing through a nozzle and in cooling the droplets obtained in a gas stream so that they solidify to give beads which are subsequently recovered and dried.

The patent document WO 2018/153913 discloses beads of at least one diphenol compound having a water content below 0.1 wt. %. Said beads are obtained from a molten composition having a water content below 0.1 wt. %. However, preparing, handling and maintaining a good stability of said composition in a molten state can prove challenging under certain conditions.

In addition, these processes require the preparation, purification or handling of hydroquinone under various conditions, notably for example drying hydroquinone in the production/purification process to very low humidity contents, melting of said hydroquinone or drying of the obtained hydroquinone beads, which can impair the coloration of said hydroquinone and thus be problematic for the use of said hydroquinone prills for some applications.

The present invention aims to provide a white or lightly colored hydroquinone prill, to overcome said disadvantages, notably providing white or lightly colored hydroquinone prills, and that offers improved handling and flowability and reduces safety, health and environmental risk to both personnel and the environment by minimizing dust and fines.

SUMMARY OF THE INVENTION

In a first aspect, the present invention relates to hydroquinone prills having a color in 5% aqueous solution of less than 250 Hazen, preferably less than 200 Hazen, more preferably less than 100 Hazen, and still more preferably less than 50 Hazen.

In another embodiment, the present invention relates to a process for the preparation of prills of hydroquinone comprising:
  a) providing a molten hydroquinone,
  b) forcing said molten composition through at least one droplet generator means to form droplets,
  c) cooling said droplets to form solid hydroquinone prills, The present invention further relates to hydroquinone prills obtainable by the process of the present invention. In another aspect, the present invention further relates to the use of said hydroquinone prills as polymerization inhibitor, anti-foulant, antioxidant, as building block for the synthesis of agrochemicals, pharmaceuticals or organic compounds or as a building block monomer for polymer production.

DETAILED DESCRIPTION OF THE INVENTION

Figure 1:
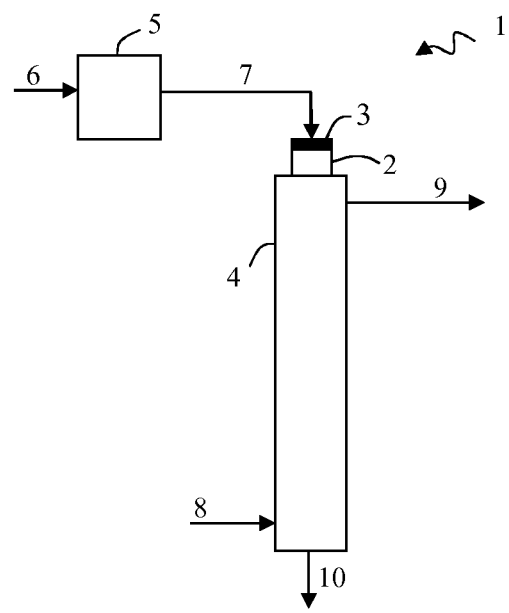
FIG. 1, FIG. 2 and FIG. 3 represent three different embodiments of a prilling device according to the invention.

In the present disclosure, unless otherwise stated, the expression "comprised between . . . and . . . " includes the limits.

One subject-matter of the present invention is hydroquinone prills having a color in 5% aqueous solution of less than 250 Hazen, preferably less than 200 Hazen, more preferably less than 100 Hazen, and still more preferably less than 50 Hazen. The hydroquinone prills may have a color in 5% aqueous solution of more than 0.1 Hazen, preferably more than 0.5 Hazen, and more preferably more than 1.0 Hazen. The color in solution is measured according to the method ASTM D1209. A solution in water comprising 5 wt % of hydroquinone is prepared for the measurement. Unless otherwise indicated, references to water shall be understood to mean reagent water conforming to Type IV of Specification D 1193.

The term "hydroquinone prills" means that the content of hydroquinone is of at least 50 wt. %, preferably at least 75 wt. %, and more preferably at least 90 wt. %.

The term "prill" refers to a solid form which is substantially spherical. A prill is therefore a solid with a high sphericity, however it is not perfectly spherical. It is also not excluded that the prill contains a "blow hole" which forms during the process for the preparation of the prills.

In a particular aspect, the water content of said hydroquinone prills is from 0.1 wt. % to 10 wt. %, preferably lower than 5 wt. %, preferably lower than 2.5 wt. %, more preferably lower than 2.0 wt. % and more preferably from 0.1 wt. % to 1 wt. %. The water content of the prills may be determined using Karl Fischer titration method. Accordingly the molten hydroquinone used in this process is not an aqueous solution of hydroquinone.

In a particular aspect, the hydroquinone prills can have an internal porosity from 0.1 cm$^3$/g to 0.75 cm$^3$/g, preferably from 0.1 cm$^3$/g to 0.5 cm$^3$/g, and more preferably from 0.1 cm$^3$/g to 0.4 cm$^3$/g. The internal porosity is determined using a mercury porosimeter Autopore IV from Micromeritics according to the method ASTM Standards on catalysts D 4284-92.

In a particular aspect, the hydroquinone prills can have a particle size distribution (PSD) where at least 50% of particle have a size between 300 μm and 2000 μm, preferably from 60% to 98%, preferably from 70% to 98%. The PSD may be determined by a sieve method or using a Malvern Mastersizer 3000 laser granulometer in wet or dry mode (Scirocco dispersion of the dry particles). Accordingly a sieve is used and the amount of particle that passes though the sieve is determined, the PSD represents the ratio between the amount of particle that passes through the sieve and the initial amount of particles.

In another aspect, the hydroquinone prills have a particle size, expressed by the mean particle diameter ($d_{50}$), in the range 300 μm to 1 cm, preferably between 400 μm and 5000 μm, more preferably between 500 μm and 3000 μm and still more preferably between 800 μm and 2000 μm. The mean particle diameter ($d_{50}$) is defined as being such that 50% by mass of the particles have a diameter greater than the median diameter and 50% by mass of the particles have a diameter smaller than the median diameter. The particle size analysis is performed on a Malvern Mastersizer 3000 laser granulometer in wet or dry mode (Scirocco dispersion of the dry particles) or directly by micrometer screw gauge.

In another aspect, the hydroquinone prills of the present invention have a loose apparent density of at least 0.3. The loose apparent density is preferably at most 0.8. In a preferred aspect the loose apparent density is between 0.5 and 0.8.

In another aspect, the hydroquinone prills of the present invention have a compact apparent density of at least 0.5. In a preferred aspect, the compact apparent density is between 0.55 and 0.90. The compact and loose apparent density are measured according to the method ASTM D 4164.

The hydroquinone prills of the present invention are far less compressible than crystallized hydroquinone powder. The compressibility of said hydroquinone prills is generally comprised between 0% to 10%, preferably from 2% to 5%. The compressibility index or Carr index is calculated by the formula:

$$\text{Carr index} = \frac{\text{Density of the compact powder} - \text{density of loose powder}}{\text{Density of the compact Powder}} \cdot 100$$

In another aspect, the hydroquinone prills of the present invention have a friability of less than 15%, preferably less than 10%, and more preferably less than 5%. The friability of the prills may be measured by mixing the prills in a triaxial mixer during 10 minutes at around 0.8 rotation per second (2 grams of prills in a 60 mL glass flask), and measuring the percentage of fine particles (ie. particles of less than 100 μm) produced. The friability is calculated as the ratio of the mass of fine particles produced over the mass of the prills introduced into the triaxial mixer.

Advantageously the hydroquinone prills of the present invention have a hardness of at least 0.7 N. Preferably the hardness is comprised between 1 N and 10 N, preferably between 1 N and 5 N, and more preferably between 1 N and 3 N. The hardness of the prills may be measured with a penetrometer also force gauge of type PCE FM-200 (manual) or Mark 10 (automatic).

Figure 4:
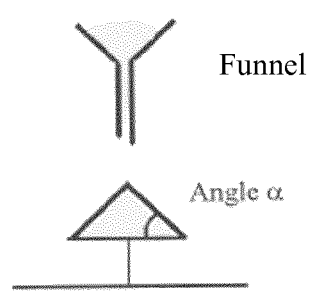
FIG. 4 shows the angle of repose.

Additionally, the hydroquinone prills of the present invention can have an angle of repose of at least 20°. Preferably the angle of repose is at most 40°. In a preferred aspect, the angle of repose is between 25° and 35°, more preferably between 28° and 32°. The angle of repose is generated by a product falling down from a funnel by gravity on a limited surface, the product will form on a conic pile and makes an angle α with the horizontal plan. Angle α represents the angle of repose (FIG. 4).

The hydroquinone prills according to the present invention can further comprise some other compounds, preferably organic compounds. Preferably the total amount of other compounds is less than 50 000 ppm, preferably less than 10 000 ppm, more preferably less than 5 000 ppm and still more preferably is less than 2 000 ppm. Preferably the amount of other compounds is more than 100 ppm, more preferably more than 200 ppm and still more preferably is more than 300 ppm. The other compounds can for example be impurities derived from the preparation process of hydroquinone, or can be added notably as antioxidant. Other compounds can preferably be selected from the group consisting of 4-hydroxy-acetophenone, resorcinol, pyrocatechol, pyrogallol, bisphenol A, para-phenoxy-phenol, isopropylhydroquinone.

In another aspect, the hydroquinone prills of the present invention can further comprise one or several other polymerization inhibitor(s) preferably selected from the group consisting of diphenol derivatives, phenol derivatives, phenothiazine, derivatives of TEMPO (2,2,6,6,tetramethyl-1-piperidine N-oxyl, or derivatives like 4-Hydroxy-2,2,6,6-tetramethylpiperidinyloxyl or 4-Oxo-2,2,6,6-tetramethyl-1-piperidinyloxyl), benzoic acid, tocopherol derivatives, vitamin E, para-benzoquinone, derivatives of phenylene diamines, aromatic nitro or nitroso derivatives, manganese complexes, preferably manganese acetate, copper complexes having an oxidation state of 2, preferably copper dibutyl dithiocarbamate or copper acetate. The total amount of other polymerization inhibitor is not particularly limited, provided the hydroquinone prills remain lightly colored. Hence the amount of added polymerization inhibitor is linked to the choice of said polymerization inhibitor. Preferably the total amount of other polymerization inhibitor is less than 50 wt. % of the composition of hydroquinone and other polymerization inhibitor, preferably less than 25 wt. %, and more preferably less than 10 wt. %.

The hydroquinone prills according to the invention generally have good dissolution properties. The dissolution properties are generally equivalent or as close as possible to the dissolution properties of other existing forms of hydroquinone. Preferably the hydroquinone prills of the invention can be dissolved in water, ethanol, acrylic acid, acrylic esters, methylmethacrylate or methacrylic acid.

In still another aspect of the present invention, the hydroquinone prills do not cake. The term "caking" or "cake" refers to the ability of a compounds to agglomerate or to form big chunks. This can be seen as a disadvantage and can mean that the compound is difficult to handle in particular for discharging or passing though pipes. Accordingly the hydroquinone of the present invention does not form such cakes, or big chunks of hydroquinone which are difficult to handle. Caking ability may be assessed by the person skilled in the art by visual inspection or by any method used for this purpose. In the present invention, caking was tested according to the following method: the test consists in taking 50 g of hydroquinone in a 250 mL closed glass vessel. The hydroquinone is stored at 50° C. for 7 days. After cooling, the glass vessel is turned upside down and the obtained hydroquinone is hit with a 80 g weight from a height (20 cm) and the number of hits to break the cake are counted. A product is described as non-caking if less than 2 hits are required to break the obtained product.

Advantageously, the amount of dust produced by the hydroquinone prills of the present invention during handling and/or discharging is very low. Preferably the amount of dust is at least reduced by 20% compared to the amount of dust produced during discharging of hydroquinone powder, more preferably reduced by at least 50%, still more preferably reduced by at least 70% and even more preferably reduced by at least 90%. A visual inspection can be carried out and shows the reduction of dust formation during handling and/or discharging.

In another embodiment, the invention relates to hydroquinone prills having a particle size distribution where at least 50% of particle have a size between 300 μm and 2000 μm.

In another embodiment, the invention relates to hydroquinone prills having an angle of repose of at least 20°. Preferably the angle of repose is at most 40°. In a preferred aspect, the angle of repose is between 25° and 35°, more preferably between 28° and 32°.

In another aspect, the invention relates to a process for the preparation of white or lightly colored hydroquinone prills according to the present invention comprising:
a) providing molten hydroquinone,
b) forcing said molten composition through at least one droplet generator means to form droplets,
c) cooling said droplets to form solid hydroquinone prills.

Step a) of the process according to the invention comprises providing molten hydroquinone.

According to one embodiment, the molten hydroquinone is prepared from a highly pure hydroquinone that is having a purity of at least 98 wt. %, more preferably at least 99 wt. %, and even more preferably of at least 99.5 wt. %.

Preferably the molten hydroquinone of step a) comprises less than 10 wt. % of water, preferably less than 5 wt. % of water, more preferably less than 2.5 wt. %, still more preferably less than 2.0 wt. % and even more preferably from 0.1 wt. % to 1 wt. %. The molten composition comprises from 0.1 wt. % to 10 wt. % of water and therefore said molten hydroquinone is not an aqueous solution of hydroquinone. Advantageously the molten hydroquinone can further comprise some other compounds. Generally the total amount of other compounds is less than 50 000 ppm, preferably less than 10 000 ppm, more preferably less than 5 000 ppm and still more preferably is less than 2 000 ppm. Preferably the amount of other compounds is more than 100 ppm, more preferably more than 200 ppm and still more preferably is more than 300 ppm. The other compounds can for example be impurities derived from the preparation process of hydroquinone, or can be added notably as antioxidant. Other compounds can preferably be selected from the group consisting of 4-hydroxy-acetophenone, resorcinol, pyrocatechol, pyrogallol, bisphenol A, para phenoxy phenol, isopropylhydroquinone.

In another aspect, the molten hydroquinone of step a) can further comprise one or several other polymerization inhibitor preferably selected from the group consisting of diphenol derivatives, phenol derivatives, phenothiazine, derivatives of TEMPO (2,2,6,6,tetramethyl-1-piperidine N-oxyl, or derivatives like 4-Hydroxy-2,2,6,6-tetramethylpiperidinyloxyl or 4-Oxo-2,2,6,6-tetramethyl-1-piperidinyloxyl), benzoic acid, tocopherol derivatives, vitamin E, para-benzoquinone, derivatives of phenylene diamines, aromatic nitro or nitroso derivatives, manganese complexes, preferably manganese acetate, copper complexes having an oxidation state of 2, preferably copper dibutyl dithiocarbamate or copper acetate. The total amount of other polymerization inhibitor is not particularly limited, provided the hydroquinone prills obtained at the end of the process remain white or lightly colored. Hence the amount of added polymerization inhibitor is linked to the choice of said polymerization inhibitor.

The hydroquinone of step a) is said to be in a molten state, which means that it is liquid enough to flow through the process devices. The compound may need to be heated so as to be in a molten form. Generally step a) is conducted at a temperature 1° C. above the melting point of hydroquinone, preferably 3° C. above the melting point of hydroquinone. Generally step a) is conducted at a temperature below 100° C. above the melting point of hydroquinone, preferably below 50° C. above the melting point of hydroquinone, more preferably below 20° C. above the melting point of hydroquinone and still more preferably 10° C. above the melting point of hydroquinone. During the heating, blanketing is preferred. The molten hydroquinone may be at least temporarily stocked into a tank provided with a system for regulating the temperature for maintaining said hydroquinone in liquid form. Preferably temperature shall be maintained as homogeneous as possible. Blanketing is preferred. The molten hydroquinone can also be directly obtained upon purification of crude hydroquinone generated by any kind of manufacturing process, especially after a distillation according to WO2008/000954.

While step a) can be operated under air under certain residence time conditions, it is preferably conducted under an inert gas, preferably under nitrogen, or oxygen-depleted air. Preferably step a) is conducted in the absence of oxygen. Without wishing to be bound by any theory, monitoring the conditions for conducting step a) can help avoiding oxidation and coloration issue of the hydroquinone while in the molten state.

Step b) of the present invention comprises forcing said molten composition through at least one droplet generator means to form droplets. The droplet generator means may be any fragmentation device, for example a turbine, a spray nozzle system or a flat plate with orifice(s) as nozzle(s).

The nozzle system used can be a single- or multi-holed with a number of holes which can be from 1 to 3000 holes, preferably between 1 and 1000 holes. It is possible to use a system comprising a plurality of nozzle plates, for example 2 nozzle plates, preferably removable, in parallel. The diameter of the nozzle plate perforations is a function of the desired prill size. It may be 100 to 1500 µm, but is preferably between 200 µm and 900 µm.

According to one embodiment, the nozzle used can be a static nozzle, but it is possible to use a nozzle subjected to a vibrating means applying a frequency of between 10 and 10 000 Hz. That device can advantageously produce droplets with a targeted size.

The molten composition is fed to the droplet generator means preferably at an overpressure ensured by a stream of inert gas, preferably a stream of nitrogen. The overpressure with respect to the atmospheric pressure is 1% to 2000%, more preferably 5% to 500%. Preferably, the temperature in the droplet generator is 0.5° C. to 50° C. above the melting point of hydroquinone, preferably 1° C. to 30° C. above the melting temperature of hydroquinone. Without wishing to be bound by any theory, it is believed that maintaining a homogeneous temperature inside the equipment heating the nozzle is helping the operations by avoiding plugging and the development of prills coloration.

The droplet generator means is preferably maintained at a temperature equal to or above the temperature at which the hydroquinone is in a molten state.

Step b) can be operated in the same conditions as step a).

Step c) of the process according to the invention comprises cooling said droplets to form solid hydroquinone prills. The cooling medium temperature is controlled and advantageously monitored. It has been noted that this parameter can impact the dustiness of the obtained prills. In addition, the cooling temperature may be maintained within a preferred range through the process. Without wishing to be bound by any theory, it is believed that the cooling temperature can influence the friability, hardness and resistance to attrition of the prills. The obtained prills therefore produce less fine particles during handling, or discharging.

According to a first embodiment, the cooling may be carried out by a cooling medium which is a cooling gas, preferably an inert gas, more preferably depleted air or nitrogen, at a temperature of between −196° C. and +150° C., preferably −100° C. and +100° C., more preferably between −40° C. and +70° C., and more preferably between −20° C. and +45° C. In this text, "depleted air" means oxygen-depleted air, for instance air comprising less than 10% of oxygen. Preferably the cooling is performed in the absence of oxygen.

Preferably, the cooling medium flows counter-currently with respect to the droplets of hydroquinone. The cold gas stream preferably leaves the tower below the nozzle at a distance representing about one tenth of the total height of the cooling zone.

The residence time, namely the period between formation of the droplet at the nozzle outlet and its arrival in the recovery system is advantageously between 0.1 second and 15 seconds, more preferably between 0.5 second and 10 seconds, and still more preferably between 0.5 second and 5 seconds.

According to a second embodiment, the cooling may be carried out by a cooling medium which is a liquefied inert gas, preferably liquid nitrogen.

Said cooling medium may preferably flow co-currently with respect to the droplets of hydroquinone. It may advantageously be introduced at the top of the cooling tower, near the droplet generator means, by the means of a liquid nitrogen spray ring.

According to a third embodiment, the cooling may be carried out by two cooling media: the droplets may be first cooled by a liquefied inert gas, preferably liquid nitrogen, and secondly by a cooling gas. Said liquefied inert gas and said cooling gas may preferably be as defined in the first and second embodiments above. Without wishing to be bound by any theory, it is believed that the liquefied inert gas may first solidify at least a fraction of the droplets, whereas the cooling gas may secondly complete the solidification of the droplets to obtain prills, which have a sufficiently solidified outer shell to withstand physical impacts on equipment, or collisions with other prills in a fluidized bed.

According to a fourth embodiment, the cooling may be carried out by two cooling media: the droplets may be first cooled by an inert gas, and secondly by a second cooling gas in another cooling part. The first and the second cooling gas may preferably be as defined in the first and second embodiment. The temperature of the second cooling gas is preferably higher than the temperature of the first cooling gas. Preferably the temperature of the first cooling gas is between −20° C. and +10° C., and the temperature of the second cooling gas is between +10° C. and +30° C.

At the end of the cooling step, solid hydroquinone prills are obtained. They may be recovered using any known means, for example under gravity in a recovery vessel or using the fluidized bed technique.

Independently to the prilling method, the solid hydroquinone prills are converted from molten hydroquinone to solid prills of hydroquinone with a conversion yield of higher than or equal to 70%, preferably higher than or equal to 80%, more preferably higher than or equal to 90% and still more preferably higher than or equal to 99%. In a specific aspect of the invention the conversion yield of the molten hydroquinone to the prills is quantitative. The conversion yield can be defined as the ratio between the weight of prills formed and the weight of the molten hydroquinone.

At the end of the process according to the invention, the amount of fine particles having a size of less than 355 µm is lower or equal to 30%, preferably lower or equal to 20%, more preferably lower or equal to 10%, still more preferably lower or equal to 1%, and even still more preferably lower or equal to 0.1% by weight of the total weight of the molten hydroquinone.

The apparatus used to carry out the process of the invention may be called a priller device.

One embodiment of the invention is represented on FIG. 1.

On FIG. 1, the priller device (1) comprises a droplet generator means (2) and a prilling tower (4). The droplet generator means (2) is provided with a vibrating means (3). The molten hydroquinone according to the invention is stocked in a heated tank (5), which maintains the composition in a molten state. A gas stream (6) (typically nitrogen) is provided to the tank (5) so that the molten hydroquinone (7) is fed to the droplet generator (3). Droplets of the molten hydroquinone fall into the prilling tower (4).

The cooling gas (8) is introduced at the bottom of the tower (4), flows counter-currently with respect to the droplets of hydroquinone, and leaves the tower at point (9) below droplet generator means (2). At the lower portion of the prilling tower (4), the prills (10) are collected.

The prilling tower (4) may be provided with any means which are typically used to allow a homogeneous distribution of the gas stream, for example baffles and screens (not shown).

According to this configuration, the upper part of the prilling tower (4) is configured for forming the prills, whereas the lower part is configured for entirely solidifying and for recovering the prills. The height of the tower (4) can vary widely, and can be determined by the skilled people according to thermal mass balance of the installation, typically between 1 and 50 meters depending on the size of the facility.

Figure 2:
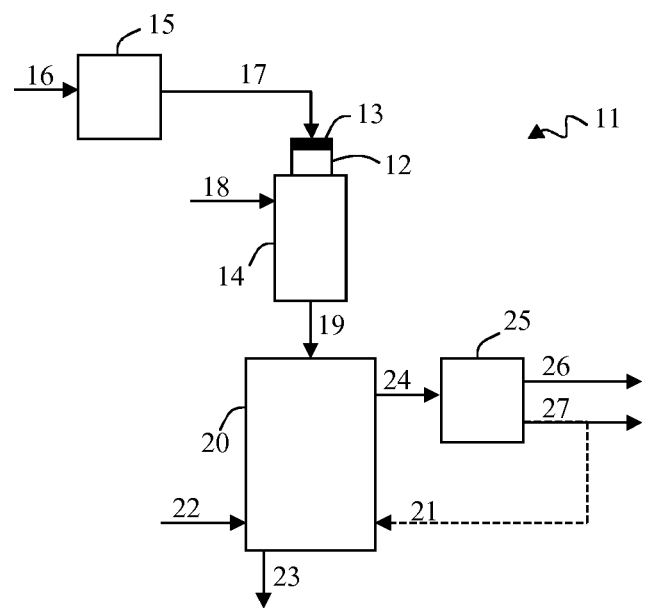

Another embodiment of the invention is represented on FIG. 2.

On FIG. 2, the priller device (11) comprises a droplet generator means (12) and a prilling tower (14). The droplet generator means (12) is provided with a vibrating means (13). The molten hydroquinone according to the invention is stocked in a heated tank (15), which maintains the hydroquinone in a molten state. A gas stream (16) (typically nitrogen) is provided to the tank (15) so that the molten hydroquinone (17) is fed to the droplet generator (12). Droplets of the molten hydroquinone fall into the prilling tower (14).

The cooling medium, which is liquid nitrogen (18) is introduced at the top of the tower (14), near the droplet generator means (12). It flows co-currently with respect to the droplets of hydroquinone. At the lower portion of the prilling tower (14), the diphenol prills (19) are collected and sent to a spiral cooler (20), wherein the solidification of the prills is completed in a fluidized bed with a countercurrent cold gaseous nitrogen stream. Said cold nitrogen stream is introduced at the bottom of the spiral cooler (20) by recycling of the nitrogen used in the prilling tower (21) and/or by fresh cold nitrogen (22).

At the lower portion of the spiral cooler (20), the prills (23) are collected.

Optionally, the gaseous nitrogen stream is removed on top (24) of the spiral cooler, together with some fine material. A cyclone (25) may be used for separating fines (26) and nitrogen (27). Nitrogen may optionally be recycled in the spiral cooler (20).

Figure 3:
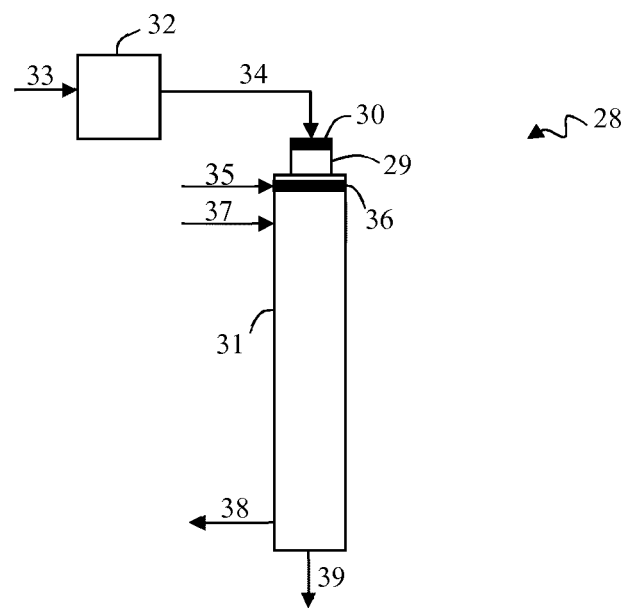

Another embodiment of the invention is represented on FIG. 3.

On FIG. 3, the priller device (28) comprises a droplet generator means (29) and a prilling tower (31). The droplet generator means (29) is provided with a vibrating means (30). The molten hydroquinone according to the invention is stocked in a heated tank (32), which maintains the composition in a molten state. A gas stream (33) (typically nitrogen) is provided to the tank (32) so that the molten composition (34) is fed to the droplet generator (29). Droplets of the molten composition fall into the prilling tower (31).

A first cooling medium, which is liquid nitrogen (35) is introduced at the top of the tower (31), near the droplet generator means (29), by the means of a liquid nitrogen spray ring (36). Said cooling medium may solidify at least a fraction of the droplets. A second cooling medium (37), which may typically be cold nitrogen stream, is introduced in the tower (31), flows co-currently with respect to the droplets hydroquinone, and leaves the tower at the bottom of the tower (38). Said second cooling medium is requested to complete the solidification of the droplets to obtain prills, which have a sufficiently solidified outer shell to withstand physical impacts on equipment, or collisions with other prills in a fluidized bed. At the lower portion of the prilling tower (31), the prills (39) are collected. Said diphenol prills may be further sent to an additional cooling means (not showed); like the spiral cooler represented on FIG. 2.

The process according to the invention may further comprise a step comprising separating fine particles by sieving or cycloning, and recycling the said fine particles. The size of the fine particles separated being less than 355 µm.

Preferably, the process according to the invention may further comprise a step comprising separating fine particles having a size of less than 100 µm, preferably by sieving or cycloning, and recycling said fine particles.

The hydroquinone prills obtainable or obtained by said process are also one subject-matter of the present invention.

EXAMPLES

Example 1: Preparation of Hydroquinone Prills According to the Invention

A prilling device as described in FIG. 1 has been used. Pure hydroquinone (containing more than 99.9 wt. % of hydroquinone) was melted at a temperature of around 200° C., under oxygen-depleted air. The cooling temperature was set at a temperature of around 10° C.

Highly spherical hydroquinone prills are obtained.

Example 2: Preparation of Hydroquinone Pearls (Comparative Example)

Hydroquinone pearls have been prepared from an aqueous solution of hydroquinone (according to the method described in WO 2004/039758).

The properties of the 2 obtained beads are compared in the Table below:

| | HQ beads according to example 1 | HQ pearls according to example 2 | HQ Powder |
|---|---|---|---|
| Color (Hazen) | 104 | 140-170 | 10 |
| % of fine particles (below 300 µm, before fine particles removal) | <0.3 | Not tested | 2 |
| Caking[1] | NO | Not tested | YES |
| Reduction of the amount of dust during discharging[2] | High | Low | 0 |
| Friability (%) | 1 | 10 | N/A |
| Internal Porosity (cm$^3$/g) | 0.22 | 0.5-0.75 | N/A |
| Average size (d$_{50}$) (µm) | 1000 | 1350 | 390 |
| Hardness (N) | 1.1 | >>1 | N/A |

[1]Place 50 g of hydroquinone in a 250 mL closed glass vessel. The hydroquinone is stored at 50° C. for 7 days. After cooling, the glass vessel is turned upside down and the obtained hydroquinone is hit with a 80 g weight from a height (20 cm). The number of hits to break the cake are counted. A product is described as non-caking if less than 2 hits are required to break the obtained product.
[2]visual inspection

The invention claimed is:

1. A process for the preparation of prills of hydroquinone comprising:
   a) providing molten hydroquinone,
   b) forcing said molten composition through at least one droplet generator means to form droplets,
   c) cooling said droplets to form solid hydroquinone prills having a color in 5% aqueous solution of less than 250 Hazen and wherein the water content is from 0.1 wt % to 10 wt %.

2. The process according to claim 1 wherein the molten hydroquinone comprises less than 10 wt. % of water.

3. The process according to claim 1, wherein the molten hydroquinone further comprises at least one other compound.

4. The process according to claim 1 wherein the molten hydroquinone further comprises at least one polymerization inhibitor.

5. The process according to claim 1 wherein steps a), b) and/or c) are conducted under inert gas, or oxygen-depleted air.

6. The process according to claim 1 wherein step a) is conducted at a temperature of 1 to 50° C. above the melting point of hydroquinone.

7. The process according to claim 1 wherein step b) is conducted at a temperature of 1 to 50° C. above the melting point of hydroquinone.

8. The process according to claim 1 wherein an overpressure of 5% to 2000% with respect to atmospheric pressure is applied in step b).

9. The process according to claim 1 wherein the cooling medium temperature is maintained at a temperature of between −196° C. and +150° C.

10. The process according to claim 1, wherein the hydroquinone prills have an internal porosity from 0.1 $cm^3/g$ to 0.75 $cm^3/g$, a loose apparent density of at least 0.3, a compact apparent density of at least 0.5, a friability of less than 15%, a hardness of at least 0.7N, or an angle of repose between 20° and 40°.

11. The process according to claim 1, wherein the hydroquinone prills have a $d_{50}$ between 0.3 mm and 1 cm.

12. The process according to claim 1, wherein the hydroquinone prills have a particle size distribution where at least 50% of particle have a size between 300 μm and 2000 μm.

13. The process according to claim 1, wherein the hydroquinone prills do not cake when stored at 50° C. during 7 days.

14. The process according to claim 1, wherein the hydroquinone prills comprise at least one other compound.

15. The process according to claim 1, wherein the hydroquinone prills comprise at least one polymerization inhibitor.

16. The process according to claim 1, wherein, when discharged, the amount of dust produced is at least reduced by 20% compared to the amount of dust produced when hydroquinone powder is discharged.

* * * * *